United States Patent [19]

Mylari et al.

[11] Patent Number: 4,723,010

[45] Date of Patent: Feb. 2, 1988

[54] PROCESS FOR PREPARING CHLOROMETHYL THIAZOLES OR OXAZOLES, AND INTERMEDIATES FOR USE THEREIN

[75] Inventors: Banavara L. Mylari, Waterford; William J. Zembrowski, Oakdale, both of Conn.

[73] Assignee: Pfizer Inc., New York, N.Y.

[21] Appl. No.: 796,359

[22] Filed: Nov. 7, 1985

[51] Int. Cl.$^4$ .................. C07D 263/56; C07D 277/64; C07D 498/04; C07D 513/04

[52] U.S. Cl. ........................... 546/114; 546/115; 544/255; 544/350; 548/152; 548/235

[58] Field of Search ............... 546/114, 115; 544/255, 544/350; 548/152, 235

[56] References Cited

U.S. PATENT DOCUMENTS

| | | | |
|---|---|---|---|
| 4,075,207 | 2/1978 | Tong | 544/350 |
| 4,550,172 | 10/1985 | Musser et al. | 548/180 |
| 4,554,355 | 11/1985 | Musser | 548/180 |

FOREIGN PATENT DOCUMENTS

52-66531  6/1977  Japan .................... 548/152

OTHER PUBLICATIONS

Hamer, J. Chem. Soc., 1480 (1956).
Saito et al, Synthesis, 102 (1979).
Musser et al, Synthetic Communications, 14(10), 947 (1984).
Okazaki et al. Chem. Abstracts, vol. 88(3) Abstract No. 24,257-g, Jan. 16, 1978.

*Primary Examiner*—Alan L. Rotman
*Attorney, Agent, or Firm*—Peter C. Richardson; Lawrence C. Akers; Gezina Holtrust

[57] ABSTRACT

Chloromethyl group substituted heterocyclic compounds of the formulae

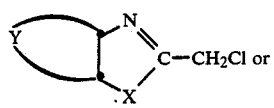

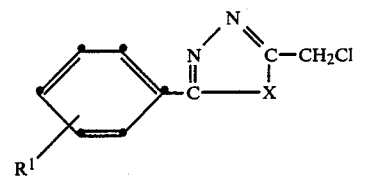

wherein
X is O or S;
Y together with the two carbons to which Y is attached forms phenyl, pyridyl or pyrimidyl, each of which may be substituted by R;
R is one of iodo or trifluoromethylthio or one or two of fluoro, chloro, bromo, ($C_1$–$C_4$)alkyl, ($C_1$–$C_4$)alkoxy, ($C_1$–$C_4$)alkylthio, ($C_1$–$C_4$)alkylsulfinyl, ($C_1$–$C_4$)alkylsulfonyl or trifluoromethyl; and
$R^1$ is hydrogen or R, are prepared by reacting a bifunctional compound of the formulae

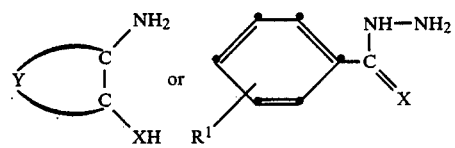

with a 2-chloro-1,1,1-tri($C_1$–$C_6$)alkoxyethane. Most of the compounds of formulae I and II are novel. These compounds are intermediates of use in the preparation of compounds having pharmaceutical activity. The 2-chloro-1,1,1-tri($C_1$–$C_6$)alkoxyethanes are prepared from the corresponding tri($C_1$–$C_6$)alkoxyethanes by chlorination with N-chlorosuccinimide or with chlorine in pyridine and a chlorohydrocarbon cosolvent.

6 Claims, No Drawings

PROCESS FOR PREPARING CHLOROMETHYL THIAZOLES OR OXAZOLES, AND INTERMEDIATES FOR USE THEREIN

BACKGROUND OF THE INVENTON

This invention relates to a process for preparing chloromethyl group substitued heterocyclic compounds of use as intermediates in the manufacture of pharmaceutically active compounds. The invention also includes novel intermediates and the preparation of 2-chloro-1,1,1-tri($C_1$–$C_6$)alkoxyethane starting materials of use in the above process.

Prior art methods for the preparation of chloromethyl group substituted heterocyclic compounds include the reaction of ortho-aminophenol with chloroacetyl chloride in Hamer, J. Chem. Soc., 1480 (1956) resulting in a very poor yield of 6%, and the reaction of orthoaminothiophenol with chlroacetyl chloride in Japanese patent publication (Kokai) 77 66531. Another method is dislcosed in Saito et al., Synthesis, 102 (1979) wherein orthoaminophenol or orthoaminothiophenol is reacted with 1-chloro-2-amino-2-ethoxyethane. This reaction proceeds with satisfactory yields. However, on substitution of the benzene ring with 4-bromo, the desired 5-bromo-2-chloromethylbenzothiazole is not formed. Similarly, desired products are not obtained on reaction with the pyridine compounds of the formula

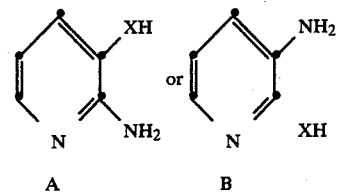

A          B wherein X is oxygen or sulphur.

According to the present process, satisfactory yields may be obtained in forming substitued and unsubstituted phenyl, pyridyl or pyrimidyl chloromethyl heterocyclics.

SUMMARY OF THE INVENTION

According to the invention, a process is provided for preparing a chloromethyl group substituted heterocyclic compound of the formulae

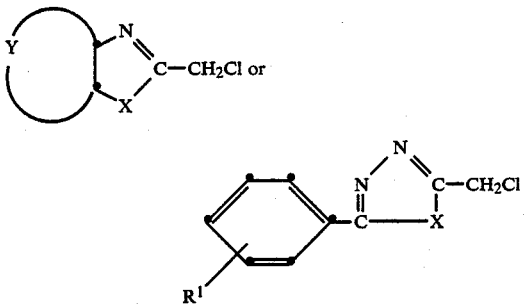

wherein X is O or S; Y together with the two carbons to which Y is attached forms phenyl, pyridyl or pyrimidyl, each of which may be substituted by R; R is one of iodo or trifluoromethylthio or one or two of fluoro, chloro, bromo, ($C_1$–$C_4$)alkyl, ($C_1$–$C_4$) alkoxy, ($C_1$–$C_4$)alkylthio, ($C_1$–$C_4$)alkylsulfinyl, ($C_1$–$C_4$)alkylsulfonyl or trifluoromethyl; and $R_1$ is hydrogen or R, by reacting a bifunctional compound of the formulae

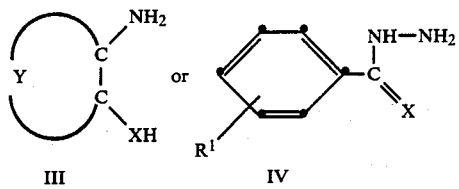

III          IV with a 2-chloro-1,1,1-tri($C_1$–$C_6$)alkoxyethane.

The invention includes novel intermediates of the formula

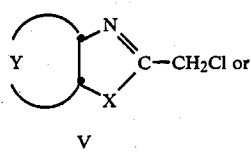

V

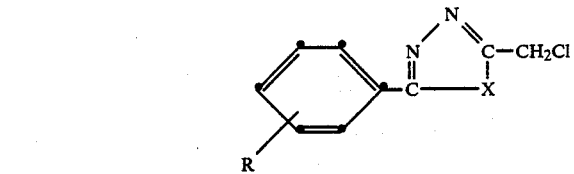

VI wherein

X is O or S; Y together with the two carbons to which Y is attached forms phenyl substituted by R; pyridyl or pyrimidyl, each of which may be substituted by R; and R is one of iodo or trifluoromethylthio or one or two of fluoro, chloro, bromo, ($C_1$–$C_4$)alkyl, ($C_1$–$C_4$)alkoxy, ($C_1$–$C_4$)alkylthio, ($C_1$–$C_4$)alkylsulfinyl, ($C_1$–$C_4$)alkylsulfonyl, or trifluoromethyl.

The invention further includes a process for preparing a 2-chloro-1,1,1-tri($C_1$–$C_6$)alkoxyethane by reacting a corresponding tri($C_1$–$C_6$)alkoxyethane with N-chlorosuccinimide or with chlorine in pyridine and a chlorohydrocarbon solvent.

The nitrogen atom in Y when Y forms pyridyl together with the two carbons to which Y is attached may be present in any position in the ring. Conveniently, the nitrogen atom is located next to the two functional groups in compound (I), as in formulae A and B above.

DETAILED DESCRIPTION OF THE INVENTION

The process for preparing the compounds of formulae I and II is conveniently carried out in a solvent. Suitable solvents are reaction inert such that they do not interfere with the reaction. Examples of suitable solvents are ($C_1$–$C_4$) alcohols such as methanol, ethanol or propanol, halocarbons such as chloroform or methylene chloride, and ethereal solvents such as diglyme. The generally preferred solvent is ethanol.

The reaction temperature ranges from about room temperature to about the reflux temperature of the solvent used. The reaction time may range from about 15 minutes to about 2 hours or more.

The intermediates of formula I when Y together with the two carbons to which it is attached forms phenyl are disclosed in the prior art such as cited above. The intermediates of formula II when $R^1$ is hydrogen are disclosed in Weidinger et al., Berichte, 96, 1049 (1963).

The starting materials of formula III are commercially available or may be made by prior art methods. Methods for preparing compounds (III) are described in J. Am. Chem. Soc. 53, 309 (1931) and J. Org. Chem. 29, 2652 (1964). In general, these methods may be depicted as follows:

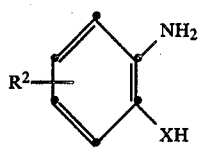

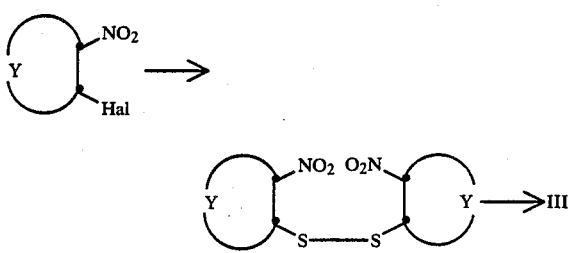

wherein Y is as defined above and Hal is fluoro or chloro.

Preferred bifunctional compounds (III) have the formula

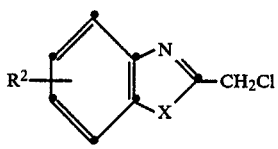

wherein $R^2$ is hydrogen, or one or two of chloro, bromo or trifluoromethyl, and X is oxygen or sulfur. Particularly preferred bifunctional compounds are 2-amino-4-bromothiophenol and 2-amino-4-trifluoromethylthiophenol. Other preferred bifunctional compounds are 2-thiol-3-aminopyridine and 2-amino-3-hydroxypyridine. These preferred and particularly preferred bifunctional compounds lead to preferred and particularly preferred, respectively, intermediates (I). Thus, preferred intermediates (I) have the formula wherein $R^2$ is hydrogen, or one or two of chloro, bromo, or trifluoromethyl, and X is oxygen or sulfur. Particularly preferred are 2-chloromethyl-5-bromobenzothiazole and 2-chloromethyl-5-trifluoromethylbenzothiazole. Also preferred are 2-chloromethyloxazolo[4,5-b]pyridine and 2-chloromethylthiazolo-[5,4-b]pyridine.

The preferred and particular preferred compounds (I) lead to preferred and particularly preferred pharmaceutical compounds described in copending application Ser. No. 796,039 filed on the same date by the same assignee as the present application now abandoned, continuation in part application Ser. No. 916,217 filed Oct. 7, 1986. These pharmaceutical compounds may be made in general by reacting compounds (I) or (II) with diazines of the formula VII as follows:

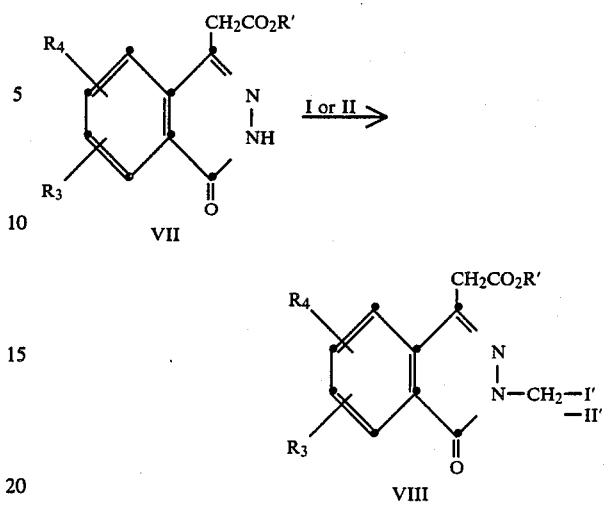

wherein I' and II' are the residues of compounds (I) and (II) remaining after reaction with compound (VII).

The hydrazines of formula IV may be made by prior art methods such as described in Jensen et al., Acta Chem. Scand. 15, 1097 (1961) forming thiohydrazides by reacting carboxymethyl dithioates and hydrazine.

The process for preparing a 2-chloro-1,1,1-tri($C_1$-$C_6$)alkoxyethane proceeds by reacting a corresponding tri ($C_1$-$C_6$)alkoxyethane with N-chlorosuccinimide, or with chlorine in pyridine and a chlorohydrocarbon solvent. The reaction with N-chlorosuccinimide is generally carried out in a solvent. Suitable solvents are non-polar, and reaction-inert such that they do not interfere with the reaction. Examples of suitable solvents are halocarbons such as chloroform, methylene chloride, carbontetrachloride or tetrachloroethylene. The reaction is conveniently carried out at about 40° C. to about the reflux temperature of the solvent. The reaction with chlorine in pyridine must be in the presence of a chlorohydrocarbon solvent having one or more chloro atoms and one to six carbon atoms, e.g. methylene chloride, chloroform, or trichloroethane.

The intermediates (I) and (II) described above are of use in the manufacture of compounds having pharmaceutical activity. Examples of such active compounds are those of above formula VIII.

The following examples illustrate the invention.

EXAMPLE 1

A mixture of 1,1,1-triethoxyethane (97.3 g) and N-chlorosuccinimide (88.1 g) in carbon tetrachloride (600 ml) was warmed to 40° C. and then irradiated with an ultraviolet lamp. The reaction became exothermic and then subsided upon completion of the reaction. The precipitated succinimide byproduct was filtered off and the filtrate was concentrated to remove carbon tetrachloride. The residual liquid was distilled to obtain pure 2-chloro-1,1,1-triethoxyethane (91.0 g; b.p. 91° C./25 mm).

EXAMPLE 2

A solution of 2-chloro-1,1,1-triethoxyethane (5.9 g) and 2-aminothiophenol (2.5 g) was heated at 80° C. for 15 minutes. After cooling to room temperature, it was dissovled in methylene chloride (30 ml) and the resulting solution was washed with 3N HCl (10 ml) and then with water (20 ml). The organic portion was evaporated and the residue chromatographed over silica gel to obtain 2-chloromethylbenzothiazole (3.35 g; 90% yield), m.p. 34° C.

EXAMPLE 3

2-Chloromethyl-5-bromobenzothiazole

A mixture of crude 2-amino-4-bromothiophenol tin hydrochloride complex (71.6 g) prepared according to JACS 53, 209 (1931), 2-chloro-1,1,1-triethoxyethane (58.7 g) and ethanol (400 ml) was heated to gentle reflux for 30 minutes to obtain a solution. To the warm solution was added 3N HCl (10 ml) and the precipitated solid was collected, washed with water and then dried to obtain the title compound (35.5 g), m.p. 107° C.

EXAMPLE 4

2-Amino-4-trifluromethylthiophenol, hydrochloride

A. The commercially available 4-chloro-3-nitrobenzotrifluroide (100 g) was dissolved in ethanol (400 ml). To this was added portionwise a solution prepared by first adding sodium sulfide hydrate (80 g) to hot ethanol (200 ml) and then sulfur (9.6 g). After the intial exothermic reaction had subsided, the reaction mixture was refluxed for an additional 30 minutes and then cooled to room temperature. The precipiated yellow solid was collected, washed with cold ethanol and then dried to yield 4,4'-ditrifluoromethyl-2,2'-dinitrodiphenyldisulfide (63.0 g; m.p. 152°–154° C.). A mixture of this compound (62 g), tin metal (20 mesh, 132.0 g), ethanol (500 ml) and concentrated HCl (200 ml) was gently refluxed at 80° C. till a near solution was obtained. Then the reaction was maintained at 70° C. for 30 minutes. The warm solution was filtered and the filtrate concentrated under low pressure to a viscous liquid. To this was added 6N HCl and the precipitated white solid was filtered to obtain the title compound (49.0 g; m.p. 208°–209° C.).

2-Chloromethyl-5-trifluoromethylbenzothiazole

B. To a solution of 2-amino-4-trifluoromethylthiophenol hydrochloride (30.0 g) in ethanol (125 ml) was added 2-chloro-1,1,1-triethoxyethane (31.0 g). The mixture was heated for 1 hour at 60° C. The solution was concentrated to remove excess ethanol and the resulting material was extracted with ether (500 ml). The organic extract was washed successively with 10% HCl (20 ml), water (100 ml), 10% sodium bicarbonate solution and water (100 ml), and then evaporated to obtain an amber colored oil, which crystallized upon standing at room temperature (28.9 g; m.p. 52° C).

EXAMPLE 5

2-Chloromethyl-oxazolo[4,5-b]pyridine

The commercially available 2-amino-3-hydroxypyridine (5.0 g) and diglyme (30 ml) were heated at 125° C. to obtain a solution. To this solution was added 2-chloro-1,1,1-triethoxyethane (9.9 g) and the mixture was held at 125° for 1 hour. The solution was cooled to room temperature and then decanted to remove a black byproduct residue. The filtrate was diluted with water (50 ml) and the resulting yellow precipitate was collected (1.5 g). A small sample was crystallized from isopropanol (m.p. 115°–118° C.).

EXAMPLE 6

2-Chloromethyl-5,7-dichlorobenzoxazole

To a solution of 2,4-dichloro-6-nitrophenol (10.0 g) in water (450 ml) containing sodium bicarbonate (4.8 g) was added sodium dithionate in a quantity sufficient to turn the original dark solution colorless. The hot reaction mixture was filtered and the filtrate was cooled to room temperature and the crystallized product, 2-amino-4,6-dichlorophenol was collected (1.6 g). The 2-amino-4,6-dichlorophenol (1.6 g) was dissolved in ethanol (5 ml) and 2-chloro-1,1,1-triethoxyethane (1.9 g) was added. The resulting solution was warmed on a steambath for 1.5 hour. After cooling to room temperature, cold water (5 ml) was added. The precipitated solid was collected and then air dried to obtain the title compound (1.12 g; m.p. 52°–53° C.).

EXAMPLE 7

2-Chloromethylthiazolo[5,4-b]pyridine

A mixture of 3-amino-2-mercaptopyridine (3.6 g) prepared by the method of J. Org. Chem., 29, 2652 (1963), 2-chloro-1,1,1-triethoxyethane (6.5 g) and ethanol (60 ml) was heated at 60° C. for 4 hours. The crude solid resulting from evaporation of ethanol was chromatographed over silica gel to obtain the product (2.94 g; m.p. 71°–73° C.).

EXAMPLE 8

2-Chloromethyl-5-bromobenzoxazole

2-Amino-4-bromophenol (1.6 g) prepared according to U.S. Pat. No. 4,157,444 was dissolved in ethanol (5 ml) and 2-chloro-1,1,1-triethoxyethane (1.9 g) was added. The resulting solution was warmed on a steambath for 1.5 hour. After cooling the reaction mixture to room temperature, cold water (5 ml) was added. The precipitated solid was collected and air-dried to obtain the product (1.12 g; m.p. 63°–65° C.

EXAMPLE 9

By a method similar to that of Example 2, 2-chloromethyl-5-chlorobenzoxazole, m.p. 53°–56° C., was prepared from commercially available 2-amino-4-chlorophenol using ethanol or chloroform as the solvent instead of methylene chloride. Similarly, 2-chloromethyl-5-methylthiobenzothiazole, m.p. 65°–66° C. and 2-chloromethyl-5-fluorobenzothiazole, m.p. 73° C., were prepared from 2-amino-4-methylthiophenol hydrochloride and 2-amino-4-fluorothiophenol hydrochloride, respectively, in ethanol solvent.

EXAMPLE 10

5-Chloromethyl-2-phenyl-1,3,4-oxadiazole

A mixture of 2-chloro-1,1,1-triethoxyethane (4.8 g), benzoyl hydrazine (3.0 g) and ethanol (30 ml) was refluxed for 2 hours and the solution was allowed to cool to room temperature. To the precipitated white crystalline solid was added water (10 ml) containing a few drops of 10% HCl. The mixture was stirred for 10 minutes, and then filtered and the solid collected. The mother liquor was evaporated to dryness, the residue triturated with water and filtered to obtain a second crop of white solid. The combined yield of the two crops amounted to 3.8 g (89%; 'HNMR identical to the product described in Chem. Ber. 96, 1049 (1969).

We claim:

1. A process for preparing a chloromethyl group substituted heterocyclic compound of the formula

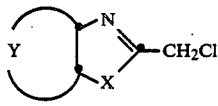

wherein

X is O or S;

Y together with the carbons to which Y is attached forms phenyl, pyridyl or pyrimidyl, each of which may be substituted by R; and R is one of iodo or trifluoromethylthio, or one or two of fluoro, chloro, bromo, ($C_1$–$C_4$)alkyl, ($C_1$–$C_4$)alkoxy, ($C_1$–$C_4$)alkylthio, ($C_1$–$C_4$)alkylsulfinyl, ($C_1$–$C_4$)alkylsulfonyl or trifluoromethyl, which comprises reacting a bifunctional compound of the formula

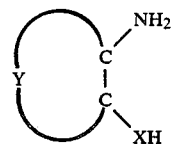

with a 2-chloro-1,1,1-tri($C_1$–$C_6$)alkoxyethane in the presence of a suitable inert solvent.

2. A process according to claim 11 wherein said reaction is carried out in ethanol.

3. A process according to claim 11 wherein said bifunctional compound has the formula

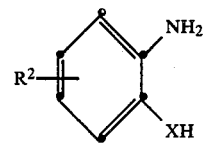

wherein $R^2$ is hydrogen, or one or two of chloro, bromo or trifluoromethyl.

4. A process according to claim 11 wherein said bifunctional compound is 2-amino-4-bromothiophenol.

5. A process according to claim 11 wherein said bifunctional compound is 2-amino-4-trifluoromethylthiophenol.

6. A process according to claim 11 wherein said bifunctional compound is 2-thiol-3-amino-pyridine or 2-amino-3-hydroxypyridine.

* * * * *